United States Patent
McGrail et al.

(10) Patent No.: US 9,403,686 B2
(45) Date of Patent: Aug. 2, 2016

(54) METHODS FOR ASSOCIATING OR DISSOCIATING GUEST MATERIALS WITH A METAL ORGANIC FRAMEWORK, SYSTEMS FOR ASSOCIATING OR DISSOCIATING GUEST MATERIALS WITHIN A SERIES OF METAL ORGANIC FRAMEWORKS, THERMAL ENERGY TRANSFER ASSEMBLIES, AND METHODS FOR TRANSFERRING THERMAL ENERGY

(71) Applicant: Battelle Memorial Institute, Richland, WA (US)

(72) Inventors: B. Peter McGrail, Richland, WA (US); Daryl R. Brown, Richland, WA (US); Praveen K. Thallapally, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 33 days.

(21) Appl. No.: 14/245,898

(22) Filed: Apr. 4, 2014

(65) Prior Publication Data

US 2014/0219901 A1 Aug. 7, 2014

Related U.S. Application Data

(62) Division of application No. 13/410,804, filed on Mar. 2, 2012, now Pat. No. 8,795,412.

(51) Int. Cl.
*B01D 53/04* (2006.01)
*F25B 17/08* (2006.01)
(Continued)

(52) U.S. Cl.
CPC ............... *C01B 31/20* (2013.01); *B01D 53/04* (2013.01); *B01J 19/087* (2013.01);
(Continued)

(58) Field of Classification Search
CPC ............. B01D 53/04; B01D 2253/204; B01D 2257/504; B01D 2259/40083; B01J 19/087; C01B 21/0427; C01B 23/0031; C01B 31/20; C01C 1/006; C01C 17/38; C01C 7/00; F25B 17/08; Y02C 10/08
USPC ........ 95/90, 114, 115; 96/115, 121, 126, 146; 62/271, 480
See application file for complete search history.

(56) References Cited

U.S. PATENT DOCUMENTS 5,085,266 A * 2/1992 Arold et al. ...................... 165/42
5,505,825 A * 4/1996 Gold et al. ....................... 95/126
(Continued)

FOREIGN PATENT DOCUMENTS

WO PCT/US2012/027458 9/2013

OTHER PUBLICATIONS

PCT/US2012/027458 Partial SR, Jun. 12, 2012, Battelle Memorial Institue.
(Continued)

*Primary Examiner* — Frank Lawrence
(74) *Attorney, Agent, or Firm* — Wells St. John P.S.

(57) ABSTRACT

Methods for releasing associated guest materials from a metal organic framework are provided. Methods for associating guest materials with a metal organic framework are also provided. Methods are provided for selectively associating or dissociating guest materials with a metal organic framework. Systems for associating or dissociating guest materials within a series of metal organic frameworks are provided. Thermal energy transfer assemblies are provided. Methods for transferring thermal energy are also provided.

16 Claims, 5 Drawing Sheets

(51) Int. Cl.
| | |
|---|---|
| C01B 31/20 | (2006.01) |
| B01J 19/08 | (2006.01) |
| C01B 21/04 | (2006.01) |
| C01B 23/00 | (2006.01) |
| C01C 1/00 | (2006.01) |
| C07C 7/00 | (2006.01) |
| C07C 17/38 | (2006.01) |
| C09K 5/00 | (2006.01) |

(52) U.S. Cl.
CPC ........ *C01B 21/0427* (2013.01); *C01B 23/0031* (2013.01); *C01C 1/006* (2013.01); *C07C 7/00* (2013.01); *C07C 17/38* (2013.01); *C09K 5/00* (2013.01); *B01D 2253/204* (2013.01); *B01D 2257/504* (2013.01); *B01D 2259/40083* (2013.01); *F25B 17/08* (2013.01); *Y02C 10/08* (2013.01); *Y02P 20/152* (2015.11)

(56) References Cited

U.S. PATENT DOCUMENTS

| | | | | |
|---|---|---|---|---|
| 5,827,355 | A * | 10/1998 | Wilson et al. | 95/114 |
| 5,972,077 | A | 10/1999 | Judkins et al. | |
| 8,425,662 | B2 * | 4/2013 | McGrail et al. | 95/139 |
| 8,795,412 | B2 * | 8/2014 | McGrail et al. | 95/90 |
| 2009/0229461 | A1 * | 9/2009 | Jeng et al. | 95/121 |
| 2010/0175557 | A1 * | 7/2010 | Shih et al. | 96/146 |
| 2010/0319534 | A1 | 12/2010 | Currier et al. | |

OTHER PUBLICATIONS

PCT-US12-027458 Search Report, Jan. 22, 2013, Battelle Memoral Institute.

PCT-US12-027458 Written Opin, Jan. 22, 2013, Battelle Memorial Institute.

Czaja et al.; "Industrial Applications of Metal-Organic Frameworks", Chemical Society Reviews, Longon, GB, vol. 38 No. 5, Mar. 16, 2009, pp. 1284-1293. (XP002602274).

Gale et al., "Organized Molecular Assemblies in the Gas Phase: Reverse Micelles and Microemulsions in Supercritical Fluids", J. Am. Chem. Soc. 109, 1987, pp. 920-921.

Glezakou et al., "Spontaneous Activation of CO2 and Possible Corrosion Pathways on the Low-Index Iron Surface Fe(100)", J. Phys. Chem. C 113(9) 2009, pp. 3691-3696.

Henninger et al., "MOF's as Adsorbents for Low Temperature Heating and Cooling Applications", J. Am. Chem. Soc 131(8) 2009, pp. 2776-2777.

Johnston et al., "Water-in-Carbon Dioxide Microemulsions: An Environment for Hydrophiles Including Proteins", Science, vol. 271, Feb. 2, 1996, pp. 624-626.

McGrail et al., "An Initial Study of Precombustion CO2 Capture Using Organic Solid Sorbents and Advanced Compression Technology", PNNL-17241, Pacific Northwest National Laboratory, Richland, Washington, 2008.

McGrail et al., "Water Reactivity in the Liquid and Supercritical CO2 Phase: Has Half the Story Been Neglected?", Energy Procedia 1(1) 2009, pp. 3415-3419.

Spycher et al., "CO2-H2O Mixtures in the Deological Sequestration of CO2: lAssessment and Calculation of Mutual Solubilities from 12 to 100 Degrees Celcius and up to 600 Bar", Geochem. Cosmochim. Ac. 67(16) 2003; pp. 3015-3031.

Thallapally et al., "Prussian Blue Analogues for CO2 and SO2 Capture and Separation Applications", Inorg. Chem. 49(11), 2010, pp. 4909-4915.

* cited by examiner

FIG. 5

METHODS FOR ASSOCIATING OR DISSOCIATING GUEST MATERIALS WITH A METAL ORGANIC FRAMEWORK, SYSTEMS FOR ASSOCIATING OR DISSOCIATING GUEST MATERIALS WITHIN A SERIES OF METAL ORGANIC FRAMEWORKS, THERMAL ENERGY TRANSFER ASSEMBLIES, AND METHODS FOR TRANSFERRING THERMAL ENERGY

CROSS REFERENCE TO RELATED APPLICATION

This application is a divisional of U.S. patent application Ser. No. 13/410,804 which was filed Mar. 2, 2012, now U.S. Pat. No. 8,795,412, entitled "Methods for Associating or Dissociating Guest Materials with a Metal Organic Framework, Systems for Associating or Dissociating Guest Materials Within a Series of Metal Organic Frameworks, Thermal Energy Transfer Assemblies, and Methods for Transferring Thermal Energy", which claims priority to U.S. Provisional Patent Application No. 61/448,965 which was filed on Mar. 3, 2011, entitled "Methods for Associating or Dissociating Guest Materials with a Metal Organic Framework, Systems for Associating or Dissociating Guest Materials Within a Series of Metal Organic Frameworks, Thermal Energy Transfer Assemblies, and Methods for Transferring Thermal Energy", the entirety of each of which is incorporated by reference herein.

STATEMENT AS TO RIGHTS TO INVENTIONS MADE UNDER FEDERALLY-SPONSORED RESEARCH AND DEVELOPMENT

This invention was made with Government support under Contract DE-AC0576RLO1830 awarded by the U.S. Department of Energy. The Government has certain rights in the invention.

TECHNICAL FIELD

The present disclosure relates to the use of metal organic frameworks.

BACKGROUND

Recently, metal organic frameworks have been proposed for use in various capacities. These capacities include but are not limited to the separation of molecules or materials from mixtures that include the molecules or materials. As an example, in various applications, metal organic frameworks have been proposed for use as materials that can be used to separate carbon dioxide from methane, for example.

In accordance with other applications, metal organic frameworks have also been utilized to retain certain molecules in higher density than they would be retained at when super pressurized. As an example, metal organic frameworks have been proposed for use as hydrogen storage tanks.

In these applications, in the past, the metal organic frameworks have been configured to selectively adsorb or desorb or associate or dissociate certain materials. As an example, the temperature and/or pressure of the metal organic framework can be manipulated, as well as the chemical and/or geometric structure of the metal organic framework, to facilitate either the association or adsorption, or the dissociation or desorption of the specific materials.

The present disclosure provides methods for using metal organic frameworks as well as systems that include metal organic frameworks and assemblies that include metal organic frameworks.

SUMMARY

Methods for releasing associated guest materials from a metal organic framework are provided with example methods including altering the oxidation state of at least a portion of the metal of the metal organic framework to dissociate at least a portion of the guest materials from the framework. Example methods for associating guest materials with a metal organic framework are also provided with example methods including altering the oxidation state of at least a portion of the metal of the metal organic framework to associate at least a portion of the guest materials with the framework.

Methods are provided for selectively associating or dissociating guest materials with a metal organic framework. Example methods can include altering the oxidation state of at least a portion of the metal of the metal organic framework to associate or dissociate at least a portion of the guest materials with the framework.

Systems for associating or dissociating guest materials within a series of metal organic frameworks are provided. Example systems can include at least two individual metal organic frameworks, with one of the individual metal organic frameworks configured to dissociate guest materials, and the other configured to associate guest materials. One framework can include at least some metals of one oxidation state and the other framework can include the same metals of another oxidation state.

Thermal energy transfer assemblies are provided. Example assemblies can include a metal organic framework electrically coupled to a power source; and a heat transfer assembly associated with the metal organic framework.

Methods for transferring thermal energy are also provided. Example methods can include adsorbing or desorbing guest materials to or from a metal organic framework, the adsorbing or desorbing facilitated by changing an oxidation state of at least some of the metal within the metal organic framework. The methods can also include providing thermal communication between a fluid and one or both of the metal organic framework or the guest materials, with the fluid changing temperature upon communication with the one or both of the metal organic framework or the guest materials.

BRIEF DESCRIPTION OF THE DRAWINGS

Embodiments of the disclosure are described below with reference to the following accompanying drawings.

DESCRIPTION

This disclosure is submitted in furtherance of the constitutional purposes of the U.S. Patent Laws "to promote the progress of science and useful arts" (Article 1, Section 8).

Figure 1:
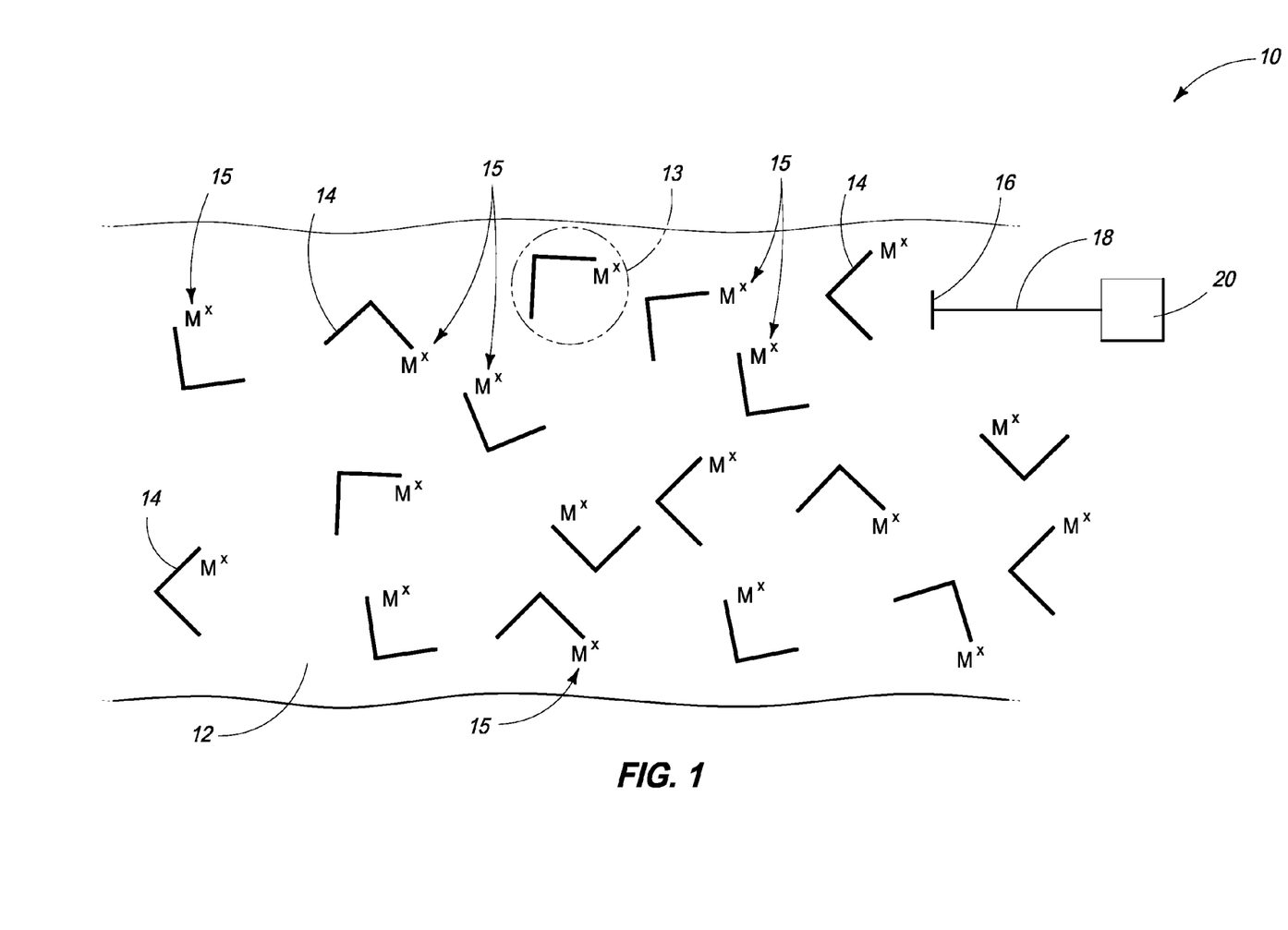
FIG. 1 is a configuration of a metal organic framework according to an embodiment of the disclosure.

The methods, systems, and assemblies of the present disclosure will be described with reference to FIGS. 1-5. Referring first to FIG. 1, a metal organic framework configuration 10 is shown that includes metal organic framework 12 conductively coupled via contact 16 and conductive conduit 18 to power source 20. Framework 12 can include metals coupled to organic components. Framework 12 may be configured to define open sites designed to receive guest materials. The open sites may be defined by more than one metal organic complex, for example. At least a portion of the metals of the metal organic framework should be electrically responsive, and more than one metal may be included in metal organic complex 13 having organic portion 14 and metal portion 15.

Metal portion 15 of complex 13 can include metals and, according to example implementations, the oxidation state of at least some of the metals will change upon application of differing voltages to the framework. The metals can include transition state metals. Example metals can include Ti, Zr, Hf, Rf, V, Nb, Ta, Db, Cr, Mo, W, Sg, Mn, Tc, Re, Bh, Fe, Ru, Os, Hs, Co, Rh, Os, Hs, Co, Rh, Ir, Mt, Ni, pd, Pt, Ds, Cu, Ag, Au, Zn, and Rg. At least a portion of framework 12 can include one or more of these metals in a charged state.

For example metal portion 15 can include mixed valence metals ($M^{2+}/M^{3+}$) complexed with the organic portion; $M^{2+}$=Fe, Cd, Co, Cu, Mn, Ni, and Zn; and $M^{3+}$=Fe or Co, for example. According to specific implementations, the metal portion can include ($Fe^{2+}/Fe^{3+}$), and this metal may be complexed as $Fe_3^{2+}[Fe^{3+}(CN)_6]_2$ or $Fe_3^{3+}[Fe^{3+}(CN)_6]$, with the former being a different oxidation state than the latter under differing electrical conditions. These mixed valence metal complexes may include tetrakis[4-(pyridyl)oxamethyl]methane as an organic component, for example.

In accordance with example implementations, the organic portion 14 may be referred to as a ligand that coordinates the metal of the framework. The ligand may be multidentate, for example. The organic portion can be a conductive organic portion. Example organic portions can include but are not limited to straight chain hydrocarbon and/or aromatic rings. The metal organic complex can include metallocenes or calixarenes for example. In accordance with example implementations, the ligand of the metal organic complex can be substantially conductive. Example organic portions of the metal organic complex can include but are not limited to tetrakis[4-(pyridyl)oxamethyl]methane or p-tert-butylcalix[4]arene.

Contact 16 can be in electrical communication with at least a portion of the metal of the metal organic framework. In accordance with example implementations, contact 16 may be in electrical communication with the organic portion of the metal organic framework and the organic portion can provide electrical communication to at least a portion of the metal of the metal organic framework. Electrical input to contact 16 from power source 20 may be controlled with a controller (not shown). The controller may be programmable and/or may be coupled to a computer operating system (not shown). In accordance with example implementations, the controller may be manipulated to provide a desired voltage to framework 12, the voltage corresponding to the association/dissociation of guest materials. Utilizing the power source and the controller voltammetry as well as cyclic voltammetry can be applied to framework 12.

Framework 12 of FIG. 1 is depicted without a substrate. In accordance with example implementations, framework 12 may be associated with a substrate. In specific implementations, framework 12 may be bond to a substrate and/or supported by or within a substrate. In accordance with example configurations, framework 12 may be within a housing, such as a conduit, including tubular conduits. In accordance with other configurations, framework 12 may be supported by a substrate with the substrate being a substantially open support such as a platform, or in other configurations, framework 12 may be supported by the exterior of a conduit, such as tubular conduit configured to contain framework and/or other materials therein. In accordance with example implementations, framework 12 can be applied to or within a substrate as a thin film.

Figure 2:
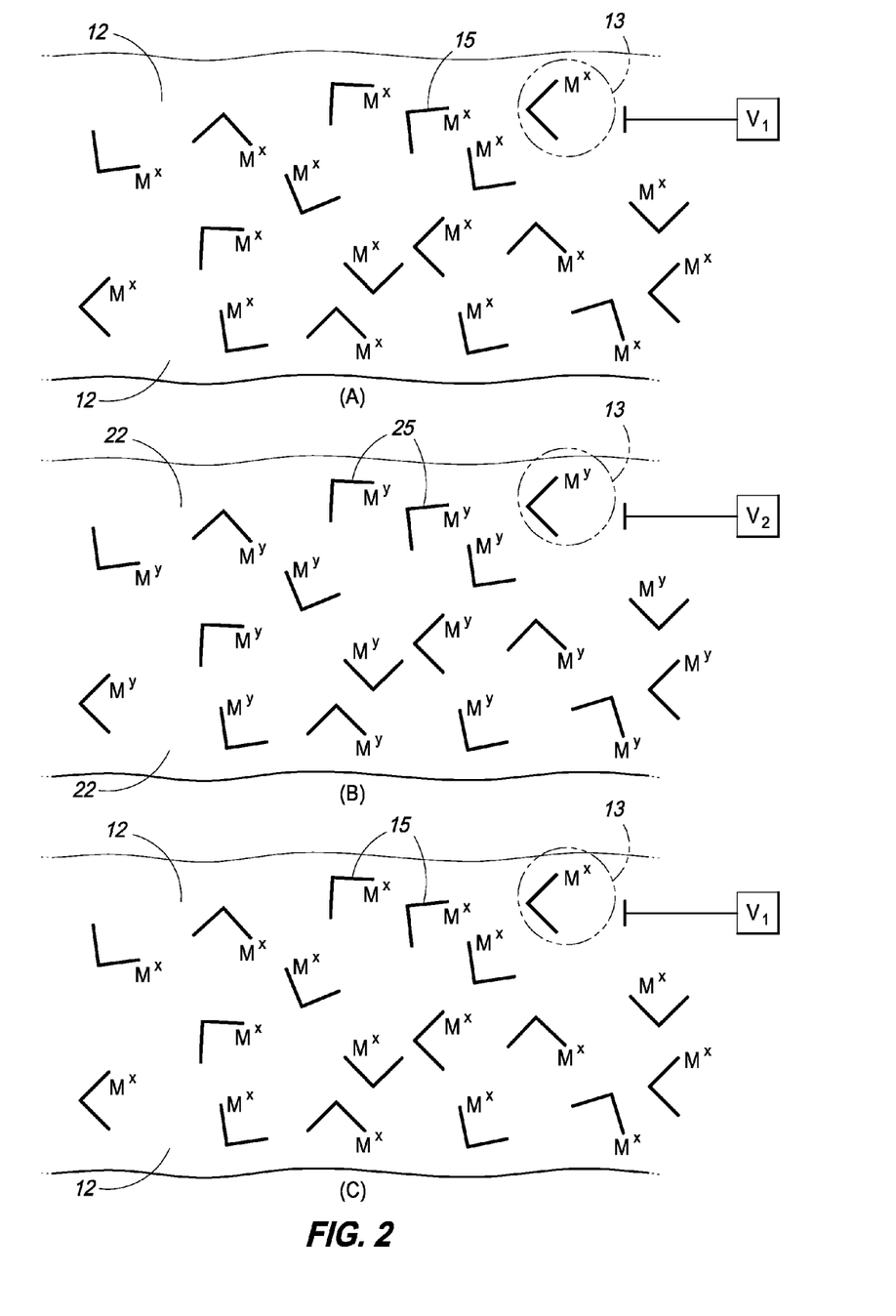
FIG. 2 represents configurations of metal organic frameworks according to an embodiment of the disclosure.

Referring next to FIG. 2, configurations of metal organic frameworks according to an embodiment of the disclosure are shown. Referring first to 2(A), framework 12 is depicted having a metal portion 15 ($M^X$), representing complex 13 having an $M^X$ oxidation state. Framework 12 has a voltage $V_1$ being applied thereto to maintain the $M^X$ oxidation state. Referring next to 2(B), framework 22 is shown having complex 13 with metal portion 25 ($M^Y$), representing the $M^Y$ oxidation state. Framework 22 has a voltage $V_2$ being applied thereto to maintain the $M^Y$ oxidation state. In accordance with example implementations, the $M^X$ oxidation state is different than the $M^Y$ oxidation state. The change in oxidation state can be facilitated by altering the voltage applied to the framework. As an example, frameworks 12 and 22 can be substantially the same, but with application of $V_1$ the oxidation state is $M^X$, and with application of $V_2$ the oxidation state is $M^Y$. In accordance with example implementations, the metal of the metal organic framework can be electrochemically altered. According to example implementations the oxidation state of at least some of the metals of the metal organic framework can be changed by altering the voltage applied to the metal and/or the metal organic framework. In example implementations $V_1$ would be different than $V_2$. Referring next to 2(C), at least a portion of the framework 12 is shown having complexes 13 including portion 15 ($M^X$) having voltage $V_1$ being applied thereto. In accordance with example implementations, framework 22 of 2(B) can be altered to reflect framework 12 of 2(C) by altering $V_2$ to $V_1$. According to specific implementations, by transitioning from 2(A)-2(C), framework 12 can transition from having metal portions 15 through metal portions 25 to metal portions 15 again.

Figure 3:
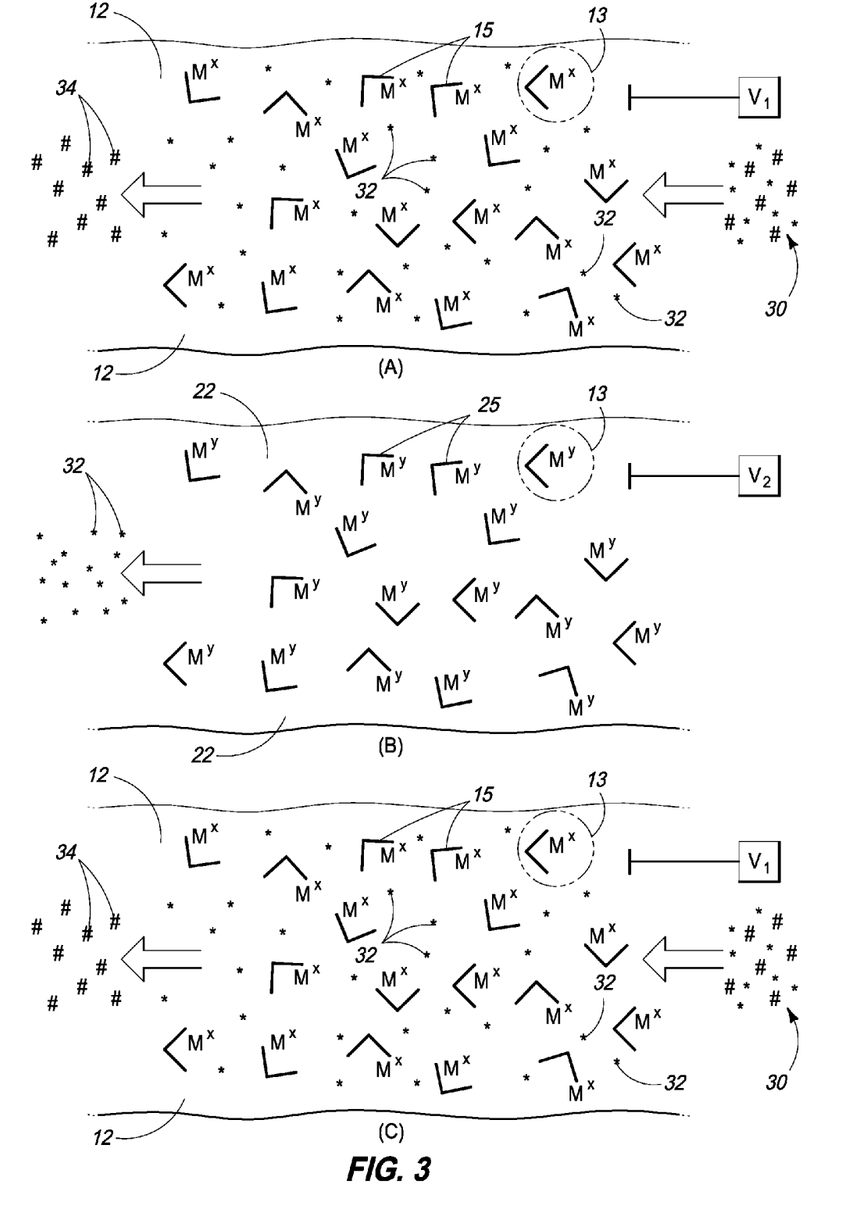
FIG. 3 represents configurations of metal organic framework and mixtures that include guest materials depicted according to an embodiment of the disclosure.

Referring next to FIG. 3, configurations of metal organic framework and mixtures that include guest materials are depicted according to an embodiment of the disclosure. Referring first to 3(A), framework 12 is shown having $V_1$ applied thereto to maintain $M^X$ oxidation states of at least some of metal portions 15 of complexes 13.

In accordance with example implementations, mixture 30 can be exposed or provided to framework 12. Mixture 30 can include guest material 32 (*). Material 32 can be a material that is desired to be separated from mixture 30. Example materials include but are not limited to carbon dioxide, and mixture 30 may include components other than carbon dioxide being represented as a remainder of the mixture 34 (#). In accordance with other implementations, guest material 32 may be exposed or provided to framework 12 in substantially pure form. For example, carbon dioxide, hydrofluorocarbons (HFC's), refrigerants, $N_2$, He, butane, propane, pentane, ammonia, and freon may be desired as a guest material and metal organic frameworks having dynamically modifiable metal portions may be configured to associate with or adsorb same.

In accordance with 3(A), mixture 30 is provided to framework 12 and at least some of material 32 is retained while material 34 is not. Accordingly, methods for associating guest materials with a metal organic framework are provided with the method including altering the oxidation state of at least a portion of the metal of the metal organic framework to associate at least a portion of the guest materials with the framework. Further, methods for exposing a mixture to the metal organic framework are provided with the mixture comprising the guest materials and other materials, and at least a portion of the other materials not being associated with the metal organic framework upon the exposing. Referring to 3(B), $V_2$ can be applied to form framework 22 from framework 12 with framework 22 including complexes 13 having metal portions 25 ($M^y$). Upon changing at least some of the oxidation state of $M^X$ to $M^y$, at least some of guest material 32 dissociates or desorbs from framework 22 as substantially pure guest material 32. Accordingly, a method for releasing associated guest materials from a metal organic framework is provided with the method including altering the oxidation state of at least a portion of the metal of the metal organic framework to dissociate at least a portion of the guest materials from the framework. Referring to 3(C), $V_1$ can be applied to again substantially form framework 12 from framework 22 with framework 12 including complexes 13 having metal portions 15 ($M^X$). Upon returning the oxidation state of $M^y$ to $M^X$, mixture 30 can be exposed to framework 12 to associate or adsorb guest material 32 with or to framework 12.

Figure 4:
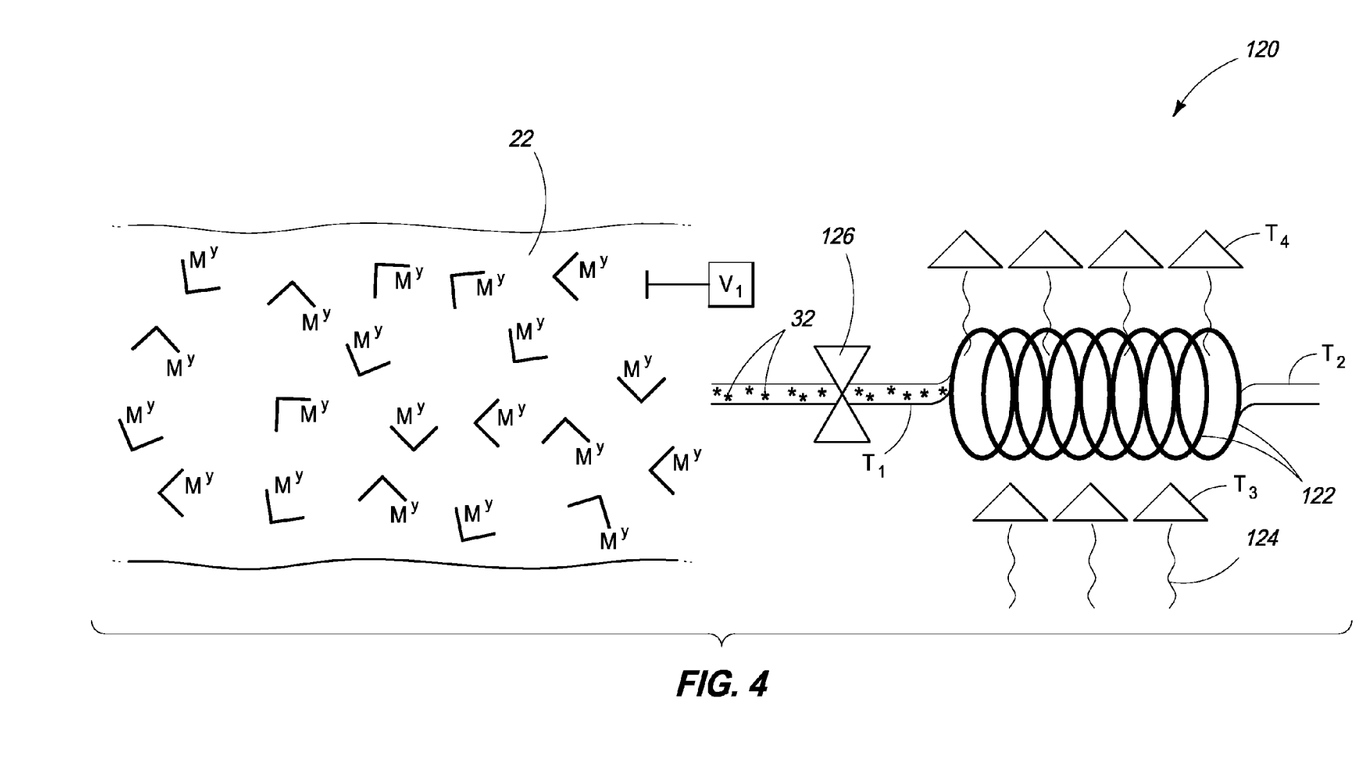
FIG. 4 represents a system including metal organic framework according to an embodiment of the disclosure.

Referring to FIG. 4, assembly 120 is shown that can be configured to transfer thermal energy. In accordance with example implementations, framework 22 can be configured to dissociate or desorb guest material 32. Guest material 32 can be such a material that when it expands from the associated or adsorbed state it consumes energy in the form of heat from its surroundings. Accordingly, guest material 32 can be provided to a heat transfer assembly such as a mass of coils 122 being configured to be exposed to fluid 124. Accordingly, temperature $T_1$ of guest material 32 can be less than temperature $T_2$ of guest material 32 after it passes through exchanger 122. Further, fluid 124 can have a temperature $T_3$ that is greater than temperature $T_4$ after being exposed to coils 122. In accordance with example implementations, framework 22 can include associated or adsorbed guest material such as a refrigerant or carbon dioxide; $V_1$ can be altered to change the oxidation state of the metal of the metal organic framework thereby dissociating or desorbing guest material from the framework. Upon dissociation the guest material can be allowed to expand via valve 126, such as a throttling valve, and be provided to coils 122 wherein the guest material cools fluid 124, such as air or water, for example. In accordance with example implementations, guest material 32 upon passing through exchanger 122 may be provided to another metal organic framework configured to associate or adsorb the guest material.

Accordingly, thermal energy transfer assemblies of the present disclosure can include a metal organic framework electrically coupled to a power source, and a heat transfer assembly associated with the metal organic framework. In accordance with specific implementations, the assemblies can further include a controller (not shown) operatively coupled to the metal organic framework and the power source. Additionally, the assembly can include another metal organic framework coupled to the heat transfer assembly, with the metal of one organic framework having an oxidation state different than the metal of the other organic framework.

Figure 5:
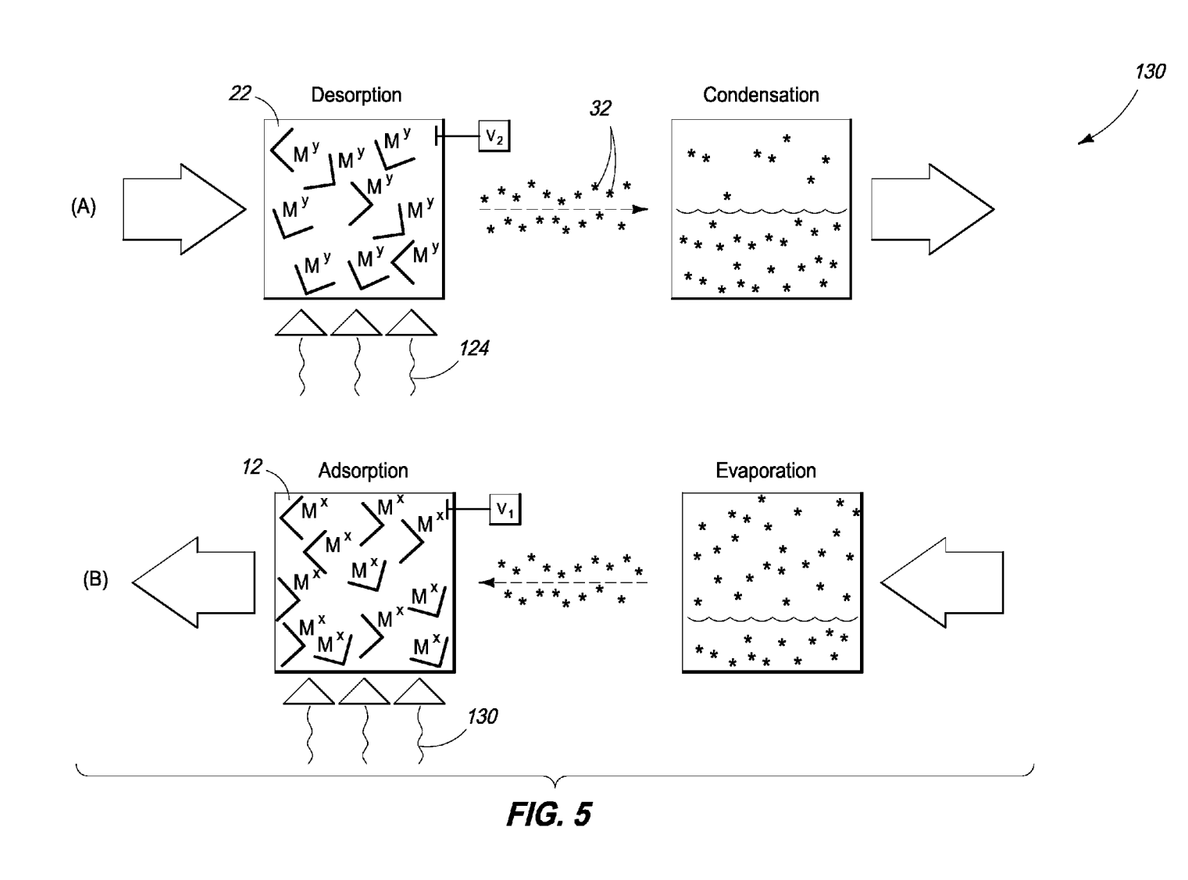
FIG. 5 represents a system including metal organic framework according to an embodiment of the disclosure.

Referring to FIG. 5, system 130 is shown generally depicting components of an adsorption chiller. Referring first to (A), guest materials 32 such as a carbon dioxide can be dissociated or desorbed upon providing $V_2$ to framework 22. During this dissociation or desorption fluid 124 can be exposed to the thermal energy of framework 22. In accordance with example implementations, framework 22 can be supported by a thermally conductive material and configured along the outside of a conduit containing fluid 124. Fluid 124 can be cooled as it passes through this conduit and utilized as desired. Further, guest material 32 can be allowed to condense.

Referring next to (B), guest material 32 can be allowed to at least partially evaporate and associate or adsorb to framework 12 at $V_1$. During adsorption, framework 12 can increase in temperature and this thermal energy may be provided to fluid 130 as it is exposed to framework 12. In accordance with example implementations, framework 12 can be configured along the outside of a conduit containing fluid 130 to facilitate the heat transfer. Accordingly, the temperature of fluid 130 upon being exposed to framework 12 can be greater than before it was exposed to framework 12. Accordingly, assembly 130 can be configured as an adsorption chiller. In accordance with example implementations, the adsorption chiller of assembly 130 includes an electrochemically driven desorption and/or adsorption cycle.

Accordingly, methods for transferring thermal energy are provided with the methods including adsorbing or desorbing guest materials to or from a metal organic framework. The adsorbing or desorbing can be facilitated by changing an oxidation state of at least some of the metal within the metal organic framework. The methods can include providing thermal communication between a fluid and one or both of the metal organic framework or the guest materials. The fluid can change temperature upon communication with the one or both of the metal organic framework or the guest materials. According to example implementations, the providing thermal communication between the metal organic framework and the liquid can include providing a conduit having an exterior in thermal contact with the metal organic framework, and providing the fluid within the conduit.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect.

The invention claimed is:

1. A method for releasing associated guest materials from a metal organic framework, the method comprising electrically altering the oxidation state of at least a portion of the metal of the metal organic framework to dissociate at least a portion of the guest materials from the framework.

2. The method of claim 1 wherein the portion of the metal of the metal organic framework is a transition metal.

3. The method of claim 1 wherein the portion of the metal of the metal organic framework is one or more of Ti, Zr, Hf, Rf, V, Nb, Ta, Db, Cr, Mo, W, Sg, Mn, Tc, Re, Bh, Fe, Ru, Os, Hs, Co, Rh, Os, Hs, Co, Rh, Ir, Mt, Ni, Pd, Pt, Ds, Cu, Ag, Au, and Rg.

4. The method of claim 1 wherein the portion of the metal of the metal organic framework has a mixed oxidation state.

5. The method of claim 1 wherein the portion of the metal of the metal organic framework is represented as ($M^{2+}/M^{3+}$).

6. The method of claim 1 wherein the portion of the metal of the metal organic framework is coupled to a substantially conductive organic ligand.

7. The method of claim 1 wherein the guest material comprises carbon dioxide.

8. A method for associating guest materials with a metal organic framework, the method comprising electrically altering the oxidation state of at least a portion of the metal of the metal organic framework to associate at least a portion of the guest materials with the framework.

9. The method of claim 8 further comprising exposing a mixture to the metal organic framework, the mixture comprising the guest materials and other materials, at least a portion of the other materials not being associated with the metal organic framework upon the exposing.

10. A method for selectively associating or dissociating guest materials with a metal organic framework, the method comprising electrically altering the oxidation state of at least a portion of the metal of the metal organic framework to associate or dissociate at least a portion of the guest materials with the framework.

11. The method of claim 10 further comprising exposing a mixture to the metal organic framework, the mixture comprising the guest materials and other materials, at least a portion of the other materials not being associated with the metal organic framework upon the exposing.

12. The method of claim 11 wherein during the exposing, guest material is associated with the metal organic framework.

13. The method of claim 12 further comprising:
ceasing the exposing;
altering the oxidation state of the portion of the metal; and
dissociating at least a portion of the guest materials from the metal organic framework.

14. The method of claim 13 further comprising:
after the dissociating, altering the oxidation state of the portion of the metal to return the oxidation state to an associating oxidation state;
after the altering, exposing the mixture to the metal organic framework; and
associating at least a portion of the guest material of the mixture with the metal organic framework.

15. The method of claim 10 wherein the altering comprises applying a predetermined voltage to the metal organic framework.

16. The method of claim 10 wherein the oxidation state of the portion of the metal is electrochemically altered.

* * * * *